(12) United States Patent
Bracht et al.

(10) Patent No.: US 8,557,279 B2
(45) Date of Patent: Oct. 15, 2013

(54) TRANSDERMAL THERAPEUTIC SYSTEM WITH CRYSTALLIZATION-INHIBITING PROTECTIVE FILM (RELEASE LINER)

(75) Inventors: Stefan Bracht, Glienicke Nordbahn (DE); Ildiko Terebesi, Berlin (DE); Thomas Langguth, Jena (DE)

(73) Assignee: Bayer Intellectual Property GmbH, Berlin (DE)

( * ) Notice: Subject to any disclaimer, the term of this patent is extended or adjusted under 35 U.S.C. 154(b) by 0 days.

(21) Appl. No.: 13/225,660

(22) Filed: Sep. 6, 2011

(65) Prior Publication Data

US 2012/0082714 A1 Apr. 5, 2012

(30) Foreign Application Priority Data

Sep. 6, 2010 (DE) .......................... 10 2010 040 299

(51) Int. Cl.
*A61F 13/00* (2006.01)
*A61K 9/70* (2006.01)
(52) U.S. Cl.
CPC ..................................... *A61K 9/703* (2013.01)
USPC .......................................................... 424/449
(58) Field of Classification Search
None
See application file for complete search history.

(56) References Cited

U.S. PATENT DOCUMENTS

| | | | |
|---|---|---|---|
| 5,128,124 A | 7/1992 | Fankhauser et al. | |
| 5,512,292 A * | 4/1996 | Gale et al. | 424/448 |
| 5,788,984 A * | 8/1998 | Guenther et al. | 424/449 |
| 2001/0009673 A1* | 7/2001 | Lipp et al. | 424/400 |
| 2003/0165547 A1* | 9/2003 | Picard-Lesboueyries et al. | 424/401 |
| 2004/0022836 A1* | 2/2004 | Degen et al. | 424/449 |
| 2005/0175678 A1 | 8/2005 | Breitenbach et al. | |
| 2006/0078604 A1* | 4/2006 | Kanios et al. | 424/449 |
| 2006/0246122 A1* | 11/2006 | Langguth et al. | 424/449 |

FOREIGN PATENT DOCUMENTS

| | | |
|---|---|---|
| EP | 0 285 563 | 10/1988 |
| EP | 1 541 137 | 6/2005 |
| WO | WO-99 66908 | 12/1999 |
| WO | WO-2004 058247 | 7/2004 |
| WO | WO-2005 058287 | 6/2005 |
| WO | WO-2010 042152 | 4/2010 |

OTHER PUBLICATIONS

Tinsorb® S product sheet by Ciba® from Ciba Specialty Chemicals, 2002, (pp. 1-24).*

* cited by examiner

*Primary Examiner* — Bethany Barham
(74) *Attorney, Agent, or Firm* — Millen, White, Zelano & Branigan, P.C.

(57) ABSTRACT

The invention relates to pharmaceutical formulations, in particular to transdermal therapeutic systems, which are characterized in that little or no active ingredient crystallizes out at the interface between the removable protective film (release liner) and the active-ingredient-containing matrix.

18 Claims, 1 Drawing Sheet

TRANSDERMAL THERAPEUTIC SYSTEM WITH CRYSTALLIZATION-INHIBITING PROTECTIVE FILM (RELEASE LINER)

The invention relates to pharmaceutical formulations, in particular transdermal therapeutic systems, which are characterized in that no active ingredient crystallizes out at the interface between removable protective film (release liner) and active-ingredient-containing matrix.

Transdermal therapeutic systems (TTS) occupy a special position among medicaments to be applied to the skin since they do not develop their effect on the skin, but via the skin. From a depot, transdermal therapeutic systems release the active ingredient into the bloodstream via the skin, as a result of which not a local, but a systemic effect is achieved. The advantage of TTS is a long-lasting effect and a constant active ingredient level which is comparable with an infusion.

Transdermal therapeutic systems (TTS) are multi-layered patches, the essential constituents of which are a covering layer which is impermeable to water, penetration promoters and active ingredients, a matrix which comprises the skin pressure-sensitive adhesive, optionally one or more penetration promoters and at least one active ingredient, and a detachable protective film (release liner).

To achieve the desired active ingredient level in the blood plasma, a high active ingredient flow through the skin is required, which is made possible either through the use of permeation promoters in transdermal systems or through high concentrations of dissolved active ingredient in the matrix of transdermal therapeutic systems.

In scientific literature, a distinction is sometimes made between permeation (passing through the skin) and penetration (penetration into the skin). In other publications, however, these terms are also used synonymously. Herein, both terms should be understood synonymously in the sense that an active ingredient passes from a transdermal system through the skin and enters the blood. The same applies analogously for the terms permeation promoter and penetration promoter.

The use of permeation promoters and also penetration promoters, which reduce the barrier function of the upper skin layer, is known particularly in the case of hormone-containing transdermal systems such as, for example, patches for contraception. On account of the limited passive skin penetration of steroid hormones such as estrogen and gestagens which are present in such contraceptive patches, in many cases penetration promoters have to be added (Sitruk-Ware, Transdermal application of steroid hormones for contraception, J Steroid Biochem Molecul Biol, Volume 53, p 247-251). The penetration promoters used are, for example, fatty acids, alcohols, PEG 400, surfactants or azones. Further substance groups which are used as penetration promoters are known to the person skilled in the art and are listed here only in extracts as examples (see also Dittgen M., Transdermale Therapeutische Systeme [Transdermal therapeutic systems]. In: Müller R H, Hildebrand G E, Ed. Pharmazeutische Technologie: Moderne Arzneiformen [Pharmaceutical Technology: Modern drug forms]. Stuttgart: Wiss Verl Ges. 81-104). Sulphoxides (DMSO), mono- and polyhydric alcohols (ethanol), alkanes, fatty acids (oleic acid), ethers (polyethylene glycols), esters, amines and amides (urea, pyrrolidone and derivatives), terpenes (limonene), cyclodextrins and surfactants.

Numerous transdermal systems which comprise gestagens and estrogens in an adhesive layer and also additionally penetration promoters are known (WO 92/07590, WO 97/397443, WO 01/37770, U.S. Pat. No. 5,512,292, U.S. Pat. No. 5,376,377, WO 90/04397, U.S. Pat. No. 6,521,250, U.S. Pat. No. 5,904,931, DE 199 06 152, WO 02/45701).

However, it is also known that the addition of permeation promoters can stress the organism in an undesired manner. For example, it can lead to skin irritations or allergic reactions.

WO 2005/058287 describes a transdermal system with an active-ingredient-containing layer which comprises a low content of hormones, specifically of gestodene and/or gestodene ester, and a support consisting of polymers such as polyisobutylene, polybutene, polyisoprene, polystyrene, styrene-isoprene-styrene block polymers, styrene-butadiene-styrene block polymers and mixtures thereof. The active-ingredient-containing layer has a solubility for gestodene of not more than 3 percent by weight, based on the active-ingredient-containing layer. The content of gestodene or gestodene ester in this layer is between 0.5 and 3 percent by weight.

High thermodynamic activities of dissolved active ingredients in the matrix of transdermal therapeutic systems are achieved in particular by so-called supersaturated systems which facilitate the desired high transdermal flow of medicaments (K. H. Ziller and H. H. Rupprecht, Pharm. Ind. 52, No. 8 (1990), 1017-1022).

Supersaturation is the term used to refer to a state in which the amount of dissolved medicament in the matrix exceeds the saturation solubility. The supersaturation of polymeric patch matrices is a simple method of increasing the skin permeation without changing the barrier properties of the Stratum corneum since the gradient of the thermodynamic activity between patch and blood is, according to Fick's law of diffusion (equation 1), the driving force for the permeation. Below the saturation concentration, the permeation is linearly dependent on the degree of saturation (this corresponds to the active ingredient concentration) (Davis & Hadgraft 1991, Pellett et al. 1994 & 1997, Megrab et al. 1995, Hadgraft 1999, Schwarb et al. 1999, Raghavan et al. 2000, Iervolino et al. 2000 & 2001). Above the saturation concentration, the thermodynamic activity is usually increased even more than the nominal concentration. Another driving force for the medicament permeation is the affinity of the medicament to the polymeric matrix and therefore the tendency to leave the patch.

The resulting supersaturated systems are either metastable or unstable and, during storage, have a tendency towards crystallization (Stefano et al. 1997, Variankaval et al. 1999, Lipp et al. 1999, Kim & Choi 2002), through which the transdermal medicament absorption can be adversely changed. This tendency towards crystallization and/or towards crystal growth is known for example in the case of suspensions and supersaturated solutions of steroid hormones (M. Kuhnert-Brandstätter et al., Sci. Pharm., 35 (1967) 4, 287-297).

This phenomenon also affects supersaturated solutions of sparingly soluble substances such as, for example, gestodene in adhesive mixtures which comprise polyisobutylene.

In the case of gestodene, it has been observed that the active ingredient crystallizes out on the protective film directly at the interface between protective film and active-ingredient-containing matrix.

On account of the crystallization process, the proportion of dissolved active ingredient decreases and crystallized active ingredient increases over time. It is known that by crystallization in some cases the concentration of the active ingredient in the system can fall even below the saturation limit (Jianwei Yu et al., Drug Development and Industrial Pharmacy 17, 1991, 1883 ff). In addition, crystal growth leads to reduction of crystal surface relative to crystal volume, as a result of which the rate of dissolution during application is reduced even further.

Since, following prolonged storage, this leads to undesirably large fluctuations in the content of dissolved active ingredient content in transdermal therapeutic systems, attempts have been made to prevent such crystallization processes in order to be able to continuously administer the therapeutically desired dose of active ingredient.

For a relatively long time it has been known that as a result of adding crystallization inhibitors, a high proportion of active ingredient remains dissolved in the matrix even after prolonged storage (WO 02/49622, WO 93/08795, WO2006/066788).

However, it is also known that the addition of crystallization inhibitors can stress the organism in an undesired manner. For example, it can lead to skin irritations or allergic reactions.

EP1490052 describes another approach for avoiding the crystallization of active ingredient, here rotigotine, from the matrix, without adding inhibitors of this type. Here, rotigotine base in crystalline form is stirred into a solution of a silicone polymer in heptane, toluene or ethyl acetate, the mixture is coated on a film and the solvent is removed by drying at 50° C. After melting the rotigotine crystals on the matrix at a temperature above the melting point of rotigotine, the active ingredient is present in the form of amorphous particles or droplets in finely divided form in the silicone-based matrix. Rotigotine is thus kept in a metastable non-crystallized condition which appears to be an unsuccessful concept judged by the fact that the Neupro® patch had to be withdrawn from the U.S.market in 2008 due to crystallization of rotigotine.

This method is only suitable for thermally stable active ingredients. In the case of temperature-labile active ingredients such as, for example, steroid hormones, reactions such as decomposition or rearrangements often arise above the melting temperature.

All of these transdermal therapeutic systems known from the prior art have the disadvantage of either
- containing crystallization inhibitors (therefore a high fraction of active ingredient remains dissolved in the matrix even after prolonged storage) or
- containing penetration promoters (therefore the desired active ingredient level in the blood plasma is achieved by a high active ingredient flow through the skin).

As is known, these additives stress the organism in addition and lead to undesired secondary reactions such as skin irritations or other allergic reactions.

It is therefore an object of the present invention to overcome the disadvantage, known from the prior art, of conventional transdermal therapeutic systems, namely the crystallization of active ingredient from the system.

This object is achieved by a solid transdermal therapeutic system in the form of a patch which contains a backing layer, at least one active-ingredient-containing matrix and a removable protective film. The transdermal therapeutic system according to the invention is characterized in that characterized in that nowhere or on less than 2% of the patch area, preferably on less than 1% of the patch area, undissolved portions of gestodene or gestodene esters precipitate out from the active-ingredient-containing adhesive matrix in the form of amorphous or crystalline particles at the interface between the removable protective film and the active-ingredient-containing matrix or within the active-ingredient-containing adhesive matrix. If crystallization is present, then it is preferred that such crystalline particles have an average diameter of at most 200 µm, preferably at most 100 µm, more preferably at most 50 µm. The transdermal therapeutic system is further characterized in that the matrix is free from solubility promoters, crystallization inhibitors and dispersants.

These active ingredient crystals are detected visually or with the help of polarization microscopy.

The transdermal therapeutic system according to the invention has, beginning with the layer furthest from the skin surface, the layer sequence backing layer (=covering film A), adhesive layer (B), separation layer (C) and finally a single- or double-layered active-ingredient-containing matrix (D), the pressure-sensitive adhesive surface of which is covered with a removable protective film (release liner E) (see FIG. 1).

According to the invention, the TTS comprises no or up to at most 5% crystallization inhibitors (based on the total mass of the active-ingredient-containing polymer matrix). If crystallization inhibitors are used, the following are used: isopropyl myristate, dimethyl isosorbide, propylene glycol, Kollidon VA 64 (available from BASF).

According to the present invention, it is preferably a transdermal therapeutic system with a single-layer active-ingredient-containing matrix.

In the transdermal therapeutic system according to the invention, the matrix has a self-adhesive design. Preferably, the self-adhesive matrix has no membrane controlling the active ingredient release. Furthermore, the matrix of the transdermal therapeutic system according to the invention comprises polymers which are selected from the group polyisobutylene, polybutene, polyacrylate, polydimethylsiloxane, styrene-isoprene block polymer or polyisoprene. Preferably the matrix comprises polyisobutylene.

The matrix comprises at least one active ingredient which is preferably selected from the group of steroid hormones.

Steroid hormones are to be understood as meaning estrogens, gestagens, antiestrogens, antigestagens, androgens, antiandrogens, glucocorticoids and mineralocorticoids.

Preferred active ingredients for the purposes of the invention are gestagens and/or estrogens.

Preferred gestagens are gestodene and derivatives thereof, such as, for example, gestodene esters. Preferred estrogens for the purposes of the present invention are ethinylestradiol, estradiol, estradiol ester.

The matrix of the transdermal therapeutic system according to the invention comprises one or more active ingredients. For example, it comprises a gestagen such as gestodene or a gestodene ester.

In a further embodiment of the present invention, the matrix comprises a combination of estrogens and gestagens. For example, the matrix of the transdermal therapeutic system according to the invention comprises ethinylestradiol and gestodene or a gestodene ester.

The active ingredients are present in the transdermal therapeutic system according to the invention in the active-ingredient-containing matrix in a concentration of 0-1.9% by weight, based on the weight of the active-ingredient-containing matrix. Preferred ranges for gestodene are 1-2%, particularly preferably 1.9%; for ethinylestradiol are 0-0.9%, particularly preferably 0.5%, based on the weight of the active-ingredient-containing matrix. In the case of a patch size of 11 cm$^2$, a patch typically comprises 2.1 mg of gestodene and 0.55 mg of EE.

The solubility of GSD and GSD esters in the active-ingredient-containing matrix is ca. 2%.

The matrix comprises the active ingredient or the active ingredients preferably in dissolved form and is typically used herewith a coating weight of 50-100 mg/10 cm² (dry weight), preferably with a coating weight of 70-100 mg/10 cm² (dry weight).

In a further embodiment of the transdermal therapeutic system according to the invention, the patch comprises a separation layer (C) and, over this, a further adhesive layer (B), in which at least one UV absorber, which is present in dissolved form in a concentration of from 0.5 to 10% (m/m), preferably 1.0 to 5.0% (m/m), particularly preferably 2.0 to 4.0% (m/m). The UV-absorber-containing adhesive layer is typically used here in a layer thickness of 10-50 mg/10 cm², preferably with a coating weight of 20-40 mg/10 cm², particularly preferably with a coating weight of 30 mg/10 cm².

Preferred UV absorbers are, for example, Tinosorb S and Tinuvin.

Preferably used UV absorbers in the transdermal therapeutic system according to the invention are Tinosorb S and Tinuvin.

Particular preference is given to Tinosorb S.

Furthermore, between the adhesive layer and the active-ingredient-containing matrix facing furthest away from the skin surface, at least one separation layer is present which is impermeable to the active ingredient. This means that the patch structure in such a case appears as follows, from the side facing furthest away from the skin: covering film, adhesive layer optionally with UV absorber, separation layer, active-ingredient-containing matrix and removable film (release liner). The separation layer of the transdermal therapeutic system according to the invention consists of a barrier polymer and preferably has a layer thickness of from 4 to 23 µm, preferably from 4 to 10 µm.

Moreover, the separation layer of the transdermal therapeutic system is impermeable to UV absorbers. Suitable barrier polymers are polyethylene terephthalate, polyacrylo-nitrile, polyvinyl chloride, polyvinylidene chloride or copolymers or colaminates thereof. In a particular embodiment of the invention, the separation layer is impermeable to UV absorbers.

The use of UV absorbers makes it possible to produce a colourless, i.e., transparent, patch, which leads to particularly high acceptance of the product by the users and improved compliance associated therewith.

For the backing layer, materials are used which are either impermeable or permeable to the contained active ingredient.

Preferably, according to the present invention, a backing layer is used which is made of active-ingredient-permeable material, such as, for example, polypropylene, polyethylene or polyurethane.

Suitable removable protective layers are all films which are customarily used in transdermal therapeutic systems. Such films are, for example, siliconized or fluoro-polymer-coated.

In order to reduce, or to avoid entirely, the above-described crystallization effect, according to the invention it is preferable that films are used which comprise the film grades FL 2000 75 µm PET 1s (78CC), FL 2000 75 µm PET 1s (RT149), FL 2000 75 µm PET 1s (RT404), Primeliner FL PET 2000 Type 78JR, Primeliner FL PET Type 78 GY (in each case available from Loparex), Perlasic LF75 (available from Perlen Converting), Scotchpak 9744, Scotchpak 9742, Scotchpak 9741 (in each case available from 3M Drug Delivery), Silphan S50 M030 (available from Siliconature), Akrosil Release Liner (available from Akrosil) or 490si (available from Adhesives Research)), Silex PET liner µ siliconized (available from Kalico Products). These films consist of an originally uncoated base film. The base film consists for example of polyethylene terephthalate (PET) or polypropylene (PP). After production, this base film is provided by the film manufacturers with a silicone or fluoro polymer coating.

Preferred release liners are Perlasic LF75, Loparex 78CC, Scotchpack 9741, Primeliner FL PET 2000 Type 78JR, Primeliner FL PET Type 78 GY and Silex PET liner µ siliconized. Most preferred release liners are Primeliner FL PET 2000 Type 78JR, Primeliner FL PET Type 78 GY and Silex PET-Folie µ (my) siliconized.

The medicament layer bordering the protective film preferably as a thickness of 100-150 µm. The active ingredients are preferably released over an area of 5 to 20 cm², preferably 7-15, particularly preferably 10-12 cm².

The transdermal therapeutic system according to the invention is preferably a patch. Patches of this type are used for example for contraception in women and comprise a gestagen, for example gestodene, in an amount of 0.5-3 mg, preferably 1-2.5 mg, particularly preferably 2.1 mg, in most cases in combination with an estrogen, for example ethinylestradiol in an amount of 0.3-0.9 mg, preferably 0.4-0.6 mg, particularly preferably 0.55 mg. Furthermore, patches which comprise hormones such as estrogens and/or gestagens are used for hormone replacement therapy and comprise an estrogen, e.g. estradiol, in an amount of 1-8, preferably 2-7.6 mg, such as e.g. in the market product Climara®, or estradiol 2-5 mg in combination with a gestagen, e.g. levonorgestrel 1-3 mg, as used e.g. in the market product Climara Pro®. The use of hormone-containing patches for oncological indications such as, for example, for estradiol substitution in the treatment of breast cancers is likewise customary (amounts 0.025-8 mg, 0.05-4 mg, 0.1-2 mg).

The transdermal therapeutic system according to the invention is preferably used for contraception.

For contraception, according to the invention, a transdermal therapeutic system is used which comprises either a steroid hormone, preferably gestodene or a gestodene ester, or a combination of gestodene with estrogens, preferably with ethinylestradiol.

Customary sizes of contraception patches are from 5 to 20 cm².

For the purposes of the invention, preference is given to a patch measuring 7-15 cm², particularly preferably 10-12 cm².

For contraception, the transdermal therapeutic system according to the invention is used for a duration of 7 days (1 week).

The patch according to the invention is used repeatedly over a period of 7 days in a cycle of 21 days (3 weeks), followed by a period of 7 days (1 week) without patch. This means that the patch according to the invention is applied to the skin on day 1, 8 and 15 within a cycle of 28 days. Preferably, the first patch according to the invention is administered on the first day of menstruation. The second is applied to the skin on day 8 calculated from the first day of menstruation, and the third is applied to the skin on day 15 calculated from the first day of menstruation.

Another embodiment of the invention consists in administering the patch on the first, second, third, fourth, fifth or sixth day after the start of menstruation.

According to a further embodiment of the invention, the patch according to the invention is administered over a period of 52 weeks by continuous administration in each case of one patch for 7 days without a patch-free period. The patch is applied for example on the first day of menstruation. The other patches are then applied in each case on day 8, 15, 22, 29, 36, 43, etc. According to the statements made above, the patch can also be administered on the first, second, third, fourth, fifth or sixth day after the start of menstruation. The application of the second then takes place accordingly on day 8, 9, 10, 11, 12 or 13 after the start of menstruation. Administration of the third and further patches then always takes place at an interval of 7 days calculated from the application of the previous patch.

Following the 52 weeks, no patch according to the invention is in turn administered over a period of 7 days.

A continuous administration of the patch according to the invention can likewise take place over a shorter period, for example 11, 13 or 26 weeks plus then in each case 7 days without patch. This means the administration of several types of the patch according to the invention takes place over a period of 11 weeks followed by a period of 7 days without patch or
13 weeks followed by a period of 7 days without patch or
26 weeks followed by a period of 7 days without patch or
52 weeks followed by a period of 7 days without patch.

The aforementioned administration variants take place with a transdermal therapeutic system according to the invention, which comprises either gestodene or gestodene ester alone or in combination with ethinylestradiol.

Furthermore, the invention relates to a kit comprising 1 to 52, 1 to 26, 1 to 13, patches as described herein for use over the course of a period of 52, 26 or 13 weeks, respectively, plus 7 days without patch.

A particularly preferred embodiment of the invention relates to a transdermal therapeutic system with 0.55 mg of ethinylestradiol and 2.1 mg of gestodene, which are dissolved in a single-layer matrix comprising polyisobutylene.

This embodiment further comprises a 4-6 µm-thick polyester film as separation layer, a further adhesive layer with the UV absorber Tinosorb S and a 50-80 µm-thick covering layer made of polyethylene (PE) (see FIG. 1). The active-ingredient-containing adhesive layer is protected by a siliconized or fluorine-coated polyester removable film (release liner). The preferred size of said embodiment is 11 cm$^2$.

The production of a transdermal therapeutic system according to the invention is described below by way of example, without limiting the invention thereto.

EXAMPLE 1

Preparation of the Samples for Crystallization Investigations

The preparation of the samples for the investigations into crystallization was carried out according to 3 processes:
Standard process: the active-ingredient-containing coating solution was drawn onto the removable film and dried. After drying, the barrier layer, optionally together with the further UV-absorber-containing adhesive layer and the covering layer, was laminated onto the dried adhesive layer.
Inverse coating: the active-ingredient-containing adhesive layer was drawn onto the separation layer and dried. The removable film was then laminated on.
Relaminating process: the active-ingredient-containing adhesive layer was drawn onto the Release Liner FL 2000 100 µm PET 1s (RT127) according to the standard process and dried. After laminating on the separation layer, the Release Liner FL 2000 100 µm PET 1s (RT127) was removed and exchanged for the release liner to be investigated.

EXAMPLE 2

Methods for Investigating the Samples for Crystallization

Visual Assessment:
Individual patches were evaluated visually in incident light.
Evaluation score for the crystallization by visual inspection:
0 visually no crystallization
0.5 signs of crystallization noticeable (at points)
2 visually detectable crystallization
Signs of crystallization are noticeable when crystals cover 0.5% or more of the patch area. Crystallization which covers 2% or more of the patch area can typically be detected visually without doubt.
Microscopy:
The crystal size in the patches was investigated on individual samples. The crystal size was evaluated using a microscope (Zeiss Axio Imager M1m, lens: W-Pi 1x/23, camera: AxioCam MRc 60 N-C 1" 1.0x).

EXAMPLE 3

Investigation of the Suitability of Various Release Liners as Removable Film

The results of the investigations into crystallization of the samples produced on the different release liners are summarized in Table 1.

The evaluation of the suitability of the release liner by optical evaluation was carried out by summation of the individual evaluations according to the following criteria:
0 removable film very suitable since all of the investigated samples crystal-free
0-2 removable film suitable since crystals observed only in individual cases (max. in 1 of the 3 investigated production methods)
2.5-4 removable film somewhat unsuitable since predominantly crystallization observed (in 2 of the 3 investigated production methods)
4.5-6 removable film absolutely unsuitable since crystallization observed in all investigated samples (in all 3 production methods).

To assess release liners not investigated here as to their suitability, patches are produced analogously to the procedure described here using at least two of the above-described application methods, and these are investigated as regards crystallization.

TABLE 1

Results for the investigation of the crystallization of gestodene and EE on different release liners

| | Film type | Manufacturer | Assessment | 12 m 40° C./75% r.h. Standard process | 6 m 40° C./75% r.h. Relaminating | 6 m 40° C./75% r.h. Inverse coating |
|---|---|---|---|---|---|---|
| A | FL 2000 100 µm PET 1s (RT127) | Loparex | 4 | 2 | 2 | n.a. |
| D | FL 2000 75 µm PET 1s (78CC) | Loparex | 2 | 0 | 0 | 2 |
| E | FL 2000 75 µm PET 1s (RT149) | Loparex | 0.5 | 0 | 0.5 | 0 |
| F | FL 2000 75 µm PET 1s (RT404) | Loparex | 2 | 0 | 0 | 2 |
| G | Perlasic L75 | Perlen | 4 | 2 | 2 | 0 |
| H | Perlasic LF75 | Perlen | 2 | 0 | 0 | 2 |
| I | Scotchpak 9744 | 3M | 0 | 0 | 0 | n.t. |
| J | Scotchpak 9741 | 3M | 0 | 0 | 0 | 0 |
| K | P70b/PETP/b-75µ | Laufenberg | 2.5 | 0 | 0.5 | 2 |
| L | 54b/PETP 75µ | Laufenberg | 4.5 | 2 | 2 | 1/2 |
| M | 52bv/52bv-2/PETP 50µ | Laufenberg | 6 | 2 | 2 | 2 |
| N | Silphan S50 M030 | Siliconature | 2 | n.t. | 2 | n.t |
| O | Silflu 50 MD07 | Siliconature | 4 | n.t. | 2 | 2 |
| P | Akrosil Release Liner | Akrosil | 0 | n.t. | 0 | n.t |
| Q | 490si | Adhesives Research | 0 | n.t. | 0 | 0 |

All release liners with an assessment value of at most 2 are suitable in principle for use as removable film for the described patch formulation containing gestodene and ethinylestradiol. These are in particular: FL 2000 75 µm PET 1s (78CC), FL 2000 75 µm PET 1s (RT149), FL 2000 75 µm PET 1s (RT404), Perlasic LF75, Scotchpak 9744 and Scotchpak 9741, Silphan S50 M030, Akrosil Release Liner and 490si. Perlasic LF75, Loparex 78CC and Scotchpack 9741 proved to be particularly suitable as the complete area of all investigated samples manufactured using one of these release liners was crystal-free under the experimental conditions specified above.

BRIEF DESCRIPTION OF THE DRAWING

FIG. 1 shows the structure of an embodiment of the patch in cross section:
A covering film (=backing layer),
B adhesive layer with UV absorber,
C separation layer,
D active-ingredient-containing adhesive layer,
E siliconized or fluorine-coated removable film (release liner)

The invention claimed is:

1. Solid transdermal therapeutic system with at least one active-ingredient containing matrix layer which comprises a polymer matrix supersaturated with gestodene or a gestodene ester, and optionally comprising ethinylestradiol, and a removable protective film directly adjacent to the matrix which is a silicone- or fluoropolymer-coated polyester removable film,
Wherein the fraction of gestodene or gestodene ester in the form of amorphous or crystalline particles at the interface between the removable protective film and the active-ingredient-containing matrix or in the active-ingredient-containing matrix is on less than 2% of the area of the system, and
wherein the matrix is free from solubility promoters, crystallization inhibitors and dispersants.

2. Solid transdermal therapeutic system of claim 1, wherein the limited amount of amorphous or crystalline particles which are present have an average diameter of not more than 200 µm.

3. Solid transdermal therapeutic system according to claim 1, wherein the fraction of gestodene or gestodene ester in the form of amorphous or crystalline particles at the interface between the removable protective film and the active-ingredient-containing matrix or in the active-ingredient containing matrix is on less than 1% of the area of the system.

4. Solid transdermal therapeutic system of claim 3, wherein the limited amount of amorphous or crystalline particles which are present have an average diameter of not more than 100 µm.

5. Solid transdermal therapeutic system according to claim 1, wherein the system comprises, in order: a backing layer, an adhesive layer, a separation layer, the at least one active-ingredient-containing matrix layer and the removable protective film.

6. Solid transdermal therapeutic system according to claim 5, wherein the adhesive layer comprises a UV absorber.

7. Solid transdermal therapeutic system according to claim 6, wherein the UV absorber is 2,4-bis-([4-(2'-ethylhexylxy-2-hydroxy]phenyl)-6-(4-methoxypheyl)-(1,3,5)-triazine.

8. Solid transdermal therapeutic system according to claim 1, wherein the system has gestodene present in an amount of 2.1 mg and ethinylestradiol present in an amount of 0.55 mg.

9. Solid transdermal therapeutic system according to claim 8 which has an area of 11 cm$^2$.

10. Solid transdermal therapeutic system (TTS) according to claim 1, wherein the TTS is in the form of a patch.

11. Solid transdermal therapeutic system according to claim 10 which is suitable for continuous application the skin of a patient over a period of 7 days.

12. Kit comprising 1 to 52, 1 to 26, or 1 to 13 patches as defined in claim 10 for continuous application over a period of 52, 26 or 13 weeks, respectively, in each case plus 7 days without patch.

13. Solid transdermal therapeutic system (TTS) according to claim 1, wherein the removable protective film is a silicone-coated polyester removable film.

14. Solid transdermal therapeutic system (TTS) according to claim 1, wherein the removable protective film is a fluoropolymer-coated polyester removable film.

15. Solid transdermal therapeutic system (TTS) according to claim 1, wherein the polymer matrix comprises a polymer selected from the group consisting of polyisobutylene, polybutene, polyacrylate, polydimethylsiloxane, styrene-isoprene block polymer or polyisoprene.

16. Solid transdermal therapeutic system (TTS) according to claim 1, wherein the polymer matrix comprises a polymer selected from the group consisting of polyisobutylene, polybutene, polydimethylsiloxane, styrene-isoprene block polymer or polyisoprene.

17. Solid transdermal therapeutic system (TTS) according to claim 1, wherein the polymer matrix comprises polyisobutylene.

18. Solid transdermal therapeutic system (TTS) according to claim 1, wherein the polymer matrix excludes a polymer comprising polyacrylate.

\* \* \* \* \*

UNITED STATES PATENT AND TRADEMARK OFFICE
CERTIFICATE OF CORRECTION

PATENT NO. : 8,557,279 B2
APPLICATION NO. : 13/225660
DATED : October 15, 2013
INVENTOR(S) : Stefan Bracht et al.

It is certified that error appears in the above-identified patent and that said Letters Patent is hereby corrected as shown below:

IN THE CLAIMS:

Column 10, line 51, (Claim 7), reads as follows: -- 6, wherein the UV absorber is 2,4-bis-([4-(2'-ethylhexylxy- --.

Should read: -- 6, wherein the UV absorber is 2,4-bis-([4-(2'-ethylhexyloxy- --.

Signed and Sealed this
Fourth Day of February, 2014

Michelle K. Lee
*Deputy Director of the United States Patent and Trademark Office*